United States Patent
Kuo et al.

(10) Patent No.: US 9,167,981 B2
(45) Date of Patent: Oct. 27, 2015

(54) ECG DEVICE, ECG LEAD SIGNAL GENERATING CIRCUIT, AND RELATED METHOD

(71) Applicant: MEDIATEK INC., Hsin-Chu (TW)

(72) Inventors: Jing-Lin Kuo, Taoyuan County (TW); Chien-Hua Hsu, Hsinchu County (TW); Chien-Chih Lee, Keelung (TW)

(73) Assignee: MEDIATEK INC., Science-Based Industrial Park, Hsin-Chu (TW)

( * ) Notice: Subject to any disclaimer, the term of this patent is extended or adjusted under 35 U.S.C. 154(b) by 115 days.

(21) Appl. No.: 14/048,057

(22) Filed: Oct. 8, 2013

(65) Prior Publication Data

US 2015/0099957 A1    Apr. 9, 2015

(51) Int. Cl.
*A61B 5/0408* (2006.01)
*A61B 5/0402* (2006.01)

(52) U.S. Cl.
CPC ........... *A61B 5/0408* (2013.01); *A61B 5/04028* (2013.01)

(58) Field of Classification Search
None
See application file for complete search history.

(56) References Cited

U.S. PATENT DOCUMENTS

| | | | |
|---|---|---|---|
| 4,608,987 A | 9/1986 | Mills | |
| 5,938,597 A * | 8/1999 | Stratbucker | 600/382 |
| 7,266,405 B1 | 9/2007 | Alroy | |
| 2003/0045804 A1* | 3/2003 | Brodnick | 600/509 |
| 2003/0233129 A1 | 12/2003 | Matos | |
| 2008/0064972 A1 | 3/2008 | Kwek | |
| 2012/0010515 A1 | 1/2012 | Zhou | |
| 2012/0165633 A1 | 6/2012 | Khair | |

* cited by examiner

*Primary Examiner* — Brian T Gedeon
(74) *Attorney, Agent, or Firm* — Winston Hsu; Scott Margo

(57) ABSTRACT

Embodiments of the invention disclose an ECG device, an ECG signal processing method, an ECG lead signal generating circuit, an ECG signal generating method, another ECG device, another ECG signal processing method, and an ECG electrode assembly. The ECG device has an electrode assembly and an ECG lead signal generating circuit. The electrode assembly has three cardio enclosure electrodes for acquiring three cardio enclosure voltages, respectively. The ECG lead signal generating circuit has a first precordial lead generator. The first precordial lead generator is configured to generate a first modified precordial lead according to the three cardio enclosure voltages, wherein the three cardio enclosure voltages are sufficient for generating the first modified precordial lead.

12 Claims, 2 Drawing Sheets

ECG DEVICE, ECG LEAD SIGNAL GENERATING CIRCUIT, AND RELATED METHOD

BACKGROUND

1. Technical Field

The invention relates generally to electrocardiography (ECG), and more particularly, to an ECG device, an ECG lead signal generating circuit, another ECG device, and related methods, and an ECG electrode assembly.

2. Related Art

An ECG device may generate electrical signals that indicate a person's heart activities. Each of the signals may be referred to as a lead or lead signal. By examining the waveforms of the leads with respect to time, a doctor may diagnose whether the patient has a heart disease.

Nowadays, heart disease is becoming more prevalent and is causing health problems to countries around the world. One way to deal with this problem is to use the proposed ECG devices that are not only easier to use but also less expensive.

SUMMARY

An embodiment of the invention provides an ECG device. The ECG device comprises an electrode assembly and an ECG lead signal generating circuit. The electrode assembly comprises three cardio enclosure electrodes for acquiring three cardio enclosure voltages, respectively. The ECG lead signal generating circuit comprises a first precordial lead generator. The first precordial lead generator is configured to generate a first modified precordial lead according to the three cardio enclosure voltages, wherein the three cardio enclosure voltages are sufficient for generating the first modified precordial lead.

Another embodiment of the invention provides an ECG signal processing method comprising the following steps. First, three cardio enclosure voltages are acquired from three cardio enclosure electrodes, respectively. Then, a first modified precordial lead is generated according to the three cardio enclosure voltages, wherein the three cardio enclosure voltages are sufficient for generating the first modified precordial lead.

Still another embodiment of the invention provides an ECG lead signal generating circuit. The ECG lead signal generating circuit comprises a first precordial lead generator. The first precordial lead generator is configured to generate a first modified precordial lead according to three cardio enclosure voltages, wherein the three cardio enclosure voltages are sufficient for generating the first modified precordial lead.

Another embodiment of the invention provides an ECG signal generating method comprising the following step. A first modified precordial lead is generated according to three cardio enclosure voltages, wherein the three cardio enclosure voltages are sufficient for generating the first modified precordial lead.

Still another embodiment of the invention provides an ECG device. The ECG device comprises an electrode assembly and an ECG lead signal generating circuit. The electrode assembly comprises three cardio enclosure electrodes for acquiring three cardio enclosure voltages, respectively, and a precordial electrode for acquiring a precordial voltage. The ECG lead signal generating circuit comprises a first precordial lead generator. The first precordial lead generator is configured to generate a first modified precordial lead according to the three cardio enclosure voltages but not according to the precordial voltage.

Another embodiment of the invention provides an ECG signal processing method comprising the following steps. First, three cardio enclosure voltages are acquired from three cardio enclosure electrodes, respectively, and a precordial voltage is acquired from a precordial electrode. Then, a first modified precordial lead is generated according to the three cardio enclosure voltages but not according to the precordial voltage.

The other embodiment of the invention provides an ECG electrode assembly. The ECG electrode assembly comprises three cardio enclosure electrodes for acquiring three cardio enclosure voltages, wherein six modified leads and a modified precordial lead are able to be generated according to the three cardio enclosure voltages.

Other features of the invention will be apparent from the accompanying drawings and from the detailed description which follows.

BRIEF DESCRIPTION OF THE DRAWINGS

The invention is fully illustrated by the subsequent detailed description and the accompanying drawings, in which like references indicate similar elements.

DETAILED DESCRIPTION

Figure 1:
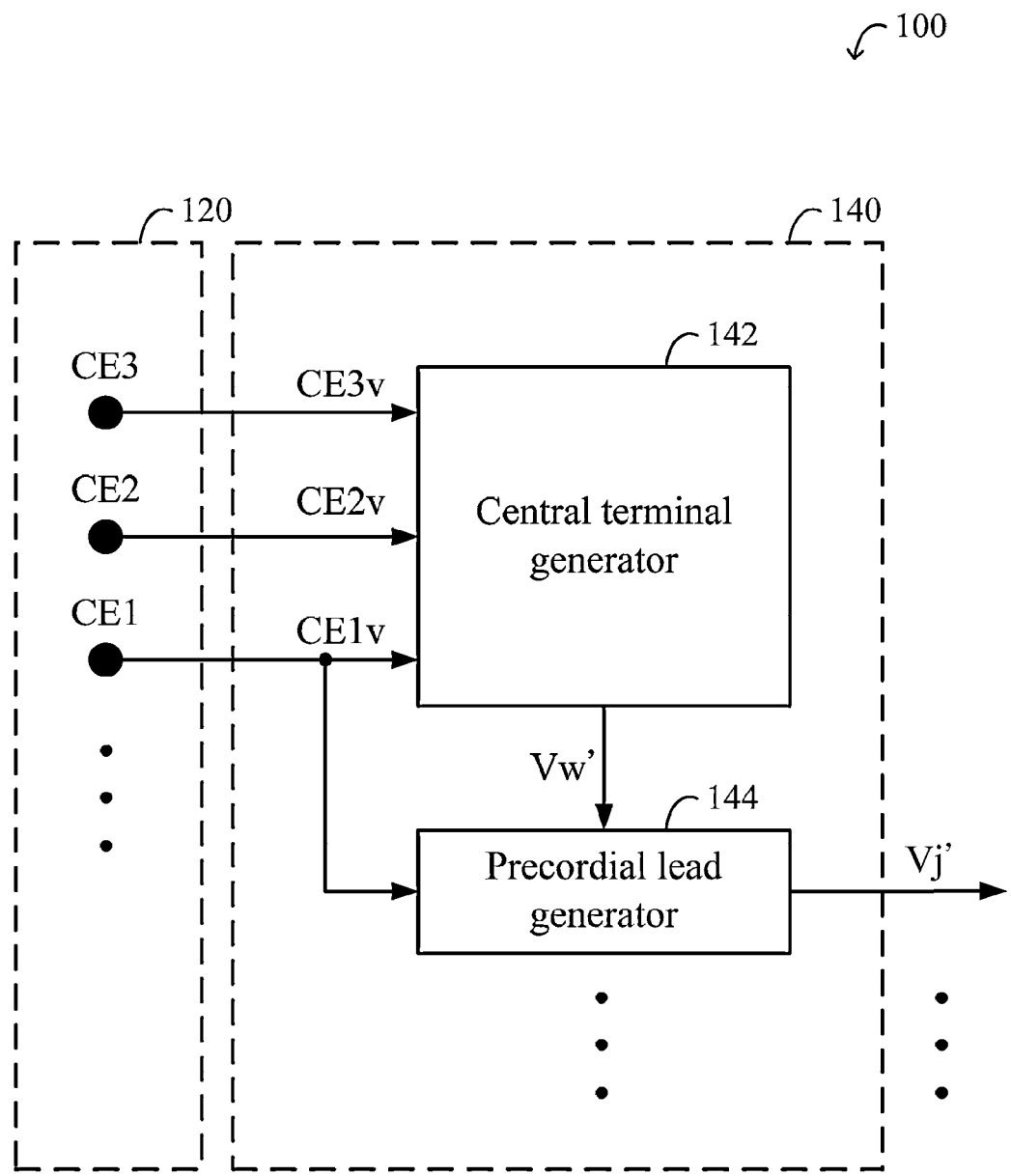
FIG. 1 shows an ECG device according to an embodiment of the invention.

FIG. 1 shows an ECG device according to an embodiment of the invention. The ECG device 100 includes an electrode assembly 120 and an ECG lead signal generating circuit 140. The electrode assembly 120 includes a plurality of electrodes to be attached to a patient's chest skin. The ECG lead signal generating circuit 140 generates at least one lead according to voltage levels of the electrodes. The ECG lead signal generating circuit 140 may pass the lead to a subsequent processor, which may then enable the waveform of the lead to be displayed or printed. The waveform may indicate the activities of the patient's heart.

In the embodiment shown in FIG. 1, the electrode assembly 120 includes at least three cardio enclosure (CE) electrodes CE1, CE2, and CE3. These three electrodes are called CE electrodes because after being attached to the patient's chest, the three CE electrodes may form a triangle that substantially encloses the patient's heart (viewing from the patient's front). Among the three CE electrodes CE1, CE2, and CE3, one that's to the right of the heart may be referred to as a CR electrode, another that's to the left of the heart may be referred to as a CL electrode, and the other that's below the heart may be referred to as a CB electrode.

In addition to the electrodes CE1, CE2, and CE3, the electrode assembly 120 may further contain some other optional electrodes not depicted in FIG. 1. For example, these optional electrodes may include a subset of a right leg drive electrode R, and precordial electrodes Ve1, Ve2, Ve3, Ve4, Ve5, and Ve6. The six precordial electrodes Ve1, Ve2, Ve3, Ve4, Ve5, and Ve6 are what conventionally used to generate six precordial leads V1, V2, V3, V4, V5, and V6 of a 12-lead ECG, respectively.

In practice, the electrode assembly 120 may be implemented in a variety of ways. For transmitting electrical signals acquired by the electrodes to the ECG lead signal generating circuit 140, conductive wires may further be incorporated as a part of the electrode assembly 120. To make the wire connections in better order, as an example, some of the connective wires may be tied in bundle style. However, in some situations wireless transmission may be adopted to eliminate the need of conductive wires and the electrode assembly 120 may employ wireless transmitting modules, for example, inside the electrodes. In this way, the ECG lead signal generating circuit 140 may perform signal processing on the electrical signals acquired by the electrodes in a remote place. It has to be emphasized that other various modifications made thereto without departing from the spirit and scope of this paragraph should all be perceived to be within the scope of the electrode assembly 120 of the invention.

Figure 2:
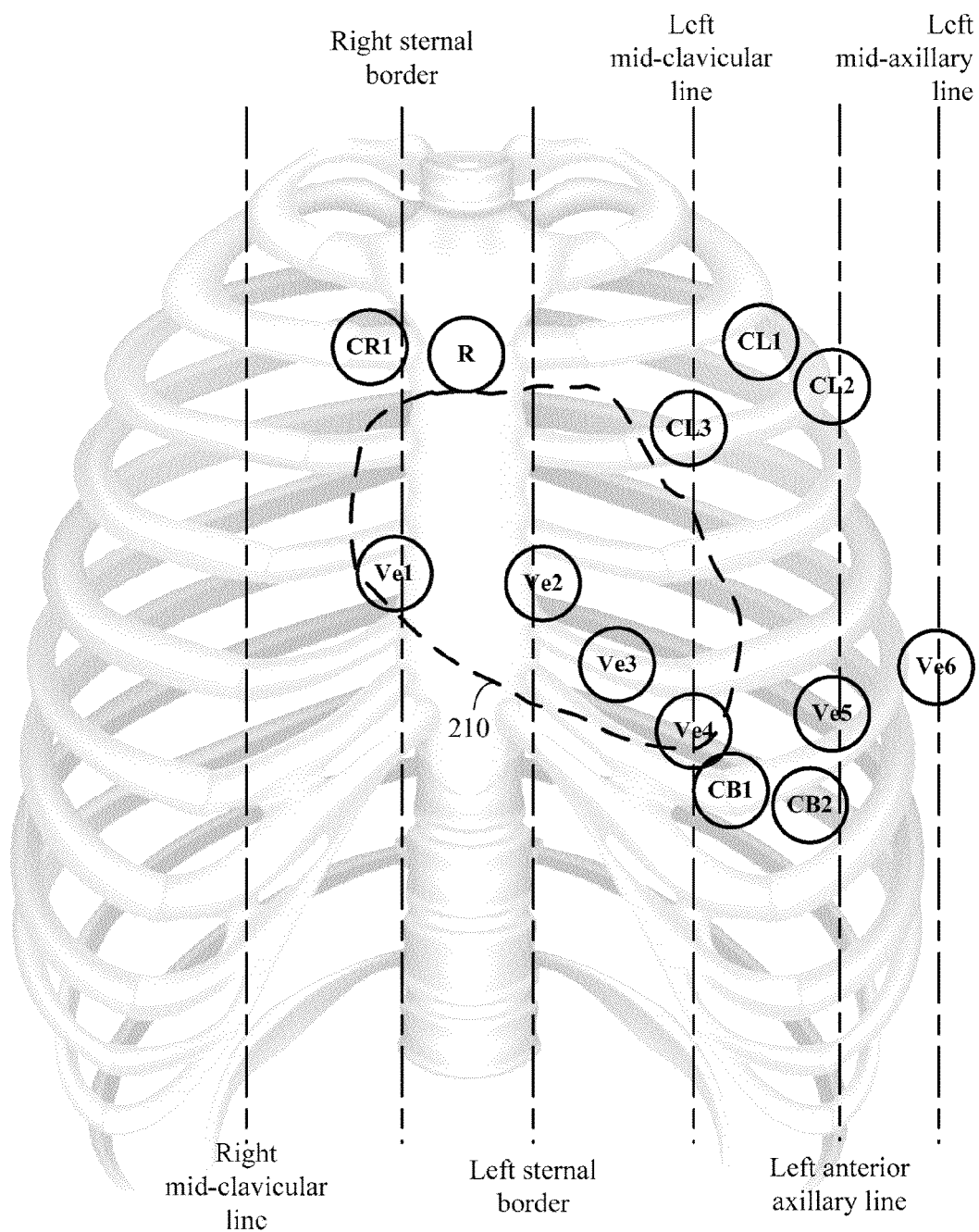
FIG. 2 shows a schematic diagram illustrating how the electrodes of the electrode assembly of FIG. 1 may be attached to a patient's chest.

FIG. 2 shows a schematic diagram illustrating how the electrodes of the electrode assembly 120 may be attached to the patient's chest. In FIG. 2, the enclosed broken line 210 represents the heart in the patient's rib cage; the straight broken lines represent some imaginary anatomy lines; the small circles represent positions on the patient's chest where electrodes of the electrode assembly 120 may be attached to.

In FIG. 2, position Ve1, CR1, or their vicinity is where the CR electrode (i.e. the right one of CE1, CE2, and CE3) may be attached to. Position CL1, CL2, CL3, or their vicinity is where the CL electrode (i.e. the left one of CE1, CE2, and CE3) may be attached to. Position Ve4, Ve5, Ve6, CB1, CB2, or their vicinity is where the CB electrode (i.e. the bottom one of CE1, CE2, and CE3) may be attached to. Positions Ve1, Ve2, Ve3, Ve4, Ve5, and Ve6 or their vicinity are where the optional precordial electrodes Ve1, Ve2, Ve3, Ve4, Ve5, and Ve6 may be attached to, respectively.

Please refer back to FIG. 1. The ECG lead signal generating circuit 140 includes a central terminal generator 142 and at least a precordial lead generator 144. Instead of using three voltages provided by a right arm (RA) electrode, a left arm (LA) electrode, and a left leg (LL) electrode to generate a Wilson's central terminal Vw in a conventional way, the central terminal generator 142 uses three voltages CE1v, CE2v, and CE3v acquired by the three electrodes CE1, CE2, and CE3 respectively to generate a modified Wilson's central terminal Vw'. For example, the central terminal generator 142 may average the three voltages CE1v, CE2v, and CE3v to generate Vw'. In other words, the central terminal generator 142 may be an average circuit and Vw' may be equal to (CE1v+CE2v+CE3v)/3.

If the CR electrode (i.e. the right one of CE1, CE2, and CE3) is attached to position Ve1 or its vicinity, it may be said that CR and Ve1 are merged as a merged electrode CRm. The merged electrode CRm may fulfill both the roles of CR and Ve1 in generating the relevant leads. Partly based on the voltage level of this merged electrode CRm, the ECG lead signal generating circuit 140 of FIG. 1 may generate not only the modified Wilson's central terminal Vw' but also a modified precordial lead Vj', as shown in FIG. 1. For example, if the electrode CE1 depicted in FIG. 1 is the CR electrode and is attached to position Ve1 depicted in FIG. 2, the precordial lead generator 144 of FIG. 1 may subtract Vw' from CE1v to generate Vj'. In other words, the precordial lead generator 144 may be a subtraction circuit and Vj' may be equal to CE1v−Vw'. In this way, the precordial electrode Ve1 for acquiring a precordial voltage Ve1v may be no longer needed since the function of Ve1v in deriving Vj' is realized by CE1v. Without the merging electrode idea presented in this paragraph, the precordial electrode Ve1 cannot be omitted in deriving Vj' since by definition Vj' equals Ve1v−Vw'.

It has to be pointed out that, through some mathematical manipulation, there are other approaches to generate Vj'. As an example, consider Vw' to be (CE1v+CE2v+CE3v)/3. With CE1v also functioning as Ve1v, Vj' (i.e. CE1v−Vw') may be formulated as (CE1v−CE2v)/3+(CE1v−CE3v)/3. As an example for generating Vj' without the central terminal generator 142, the precordial lead generator may comprise two subtractors that derive the two terms (CE1v−CE2v) and (CE1v−CE3v), respectively and one adder to sum the aforementioned two terms. Of course, one can easily come up with different formulations for deriving Vj'; however, any of such variants not departing from the spirit of the disclosure above shall be regarded to fall within the scope of the invention. Also, the formulation provided in this example may be applied to other merged electrode cases described below and will be omitted later for the sake of brevity.

Therefore, according to previous two paragraphs, it can be said that the central terminal generator 142 may be removed and the precordial lead generator 144 may generate Vj' according to CE1v, CE2v and CE3v, wherein CE1v, CE2v and CE3v are sufficient for generating Vj'. Note that using the word sufficient means the modified precordial lead, denoted as Vj1', generated according to CE1v, CE2v and CE3v but not according to Ve1v still bears similar characteristics as compared with the conventional modified precordial lead, denoted as Vj2', generated also according to Ve1v, in addition to CE1v, CE2v and CE3v. To be more specific, according to experimental results, it can be shown the morphology and level of Vj1' and Vj2' are similar. Secondly, Vj1' may also help doctors make a correct diagnosis, just as Vj2'. This suggests Vj1' generated based on the proposed merged electrode concept may be as useful as Vj2' generated according to three cardio enclosure voltage and one precordial voltage for common practical applications.

If the CB electrode (i.e. the bottom one of CE1, CE2, and CE3) is attached to one of positions Ve4, Ve5, and Ve6 or its vicinity, it may be said that CB and one of Ve4, Ve5, and Ve6 are merged as a merged electrode CBm. The merged electrode CBm may fulfill both the roles of CB and one of Ve4, Ve5, and Ve6 in generating the relevant leads. Partly based on the voltage level of this merged electrode, the ECG lead signal generating circuit 140 of FIG. 1 may generate not only the modified Wilson's central terminal Vw' but also a modified precordial lead V4', V5', or V6'. For example, if the electrode CE1 depicted in FIG. 1 is the CB electrode and is attached to position Ve4, Ve5, or Ve6 depicted in FIG. 2, the precordial lead generator 144 of FIG. 1 may subtract Vw' from CE1v to generate V4', V5', or V6', which is labeled as Vj' in FIG. 1.

If both the CR and CB electrodes are merged respectively as merged electrodes CRm and CBm, the precordial lead generator 144 of FIG. 1 may subtract Vw' from one of the merged electrodes' voltage (i.e. CE1v) to generate the modified precordial lead Vj', as also shown in FIG. 1. In addition, the ECG lead signal generating circuit 140 of FIG. 1 may further include a second precordial lead generator that subtract Vw' from the voltage of the other of the merged electrodes (CE2v or CE3v) to generate another modified precordial lead Vk'. One of the variables j and k may be equal to 1 while the other may be equal to 4, 5, or 6. Note that for the sake of brevity, the second precordial lead generator is not drawn in FIG. 1 as it is easy to conceive how it can be fit into FIG. 1.

In practice, there are several ways to implement the ECG lead signal generating circuit 140. For instance, the central terminal generator 142 and the precordial lead generator 144 may be implemented by digital signal processors (DSP), application specific ICs (ASIC) or any form of electrical circuits. Besides, the Vw' need not be sent to the precordial lead generator 144 through an electrically wired connection. For instance, the Vw' may be sent via wireless communication link so that the central terminal generator 142 and the precordial lead generator 144 may interact with each other remotely and wireless transceiver modules may be inside both of them.

Please refer to FIG. 2. Each of positions Ve1, Ve4, Ve5, and Ve6 is a potential position for a merged electrode. For example, position Ve1 is in a region of the fourth intercostal space at the right sternal border. Position Ve4 is in a region of the fifth intercostal space at the left mid-clavicular line. Position Ve5 is in a region of the fifth intercostal space at the left anterior axillary line. Position Ve6 is in a region of the fifth intercostal space at the left mid-axillary line.

Please refer back to FIG. 1. If the electrode assembly 120 has a precordial electrode Vei (where i is equal to 1, 2, 3, 4, 5, or 6) that's not merged with any of the three CE electrodes, the ECG lead signal generating circuit 140 may further include a lead signal generator that generate a modified precordial lead Vi' based on precordial voltage Veiv acquired by precordial electrode Vei and the modified Wilson's central terminal Vw'. Specifically, this lead signal generator may subtract Vw' from Veiv to generate Vi'. In other words, Vi'=Veiv−Vw'. With Vi' and the modified precordial lead Vj' depicted in FIG. 1, the ECG lead signal generating circuit 140 may generate up to six modified precordial leads.

In addition to at least one modified precordial lead, the ECG lead signal generating circuit 140 may further be configured to use voltages CRv, CLv, and CBv acquired respectively by the CR, CL, and CB electrodes to generate any of three modified limb leads I', II', and III', and any of three modified augmented limb leads aVR', aVL', and aVF'. Specifically, the ECG lead signal generating circuit 140 may do so according to any of the following six equations.

$$I'=CLv-CRv$$

$$II'=CBv-CRv$$

$$III'=CBv-CLv$$

$$aVR'=CRv-(CLv+CBv)/2=(I'+II')/2$$

$$aVL'=CLv-(CRv+CBv)/2=I'-II'/2$$

$$aVF'=CBv-(CRv+CLv)/2=II'-I'/2$$

The ECG lead signal generating circuit 140 may be pure hardware. For example, it may include hardware average circuits and hardware subtraction circuits but no processors. Being pure hardware, the cost of the ECG lead signal generating circuit 140 may be relatively lower. In addition, the pure hardware does not generate leads through synthesis; instead, it generates leads directly based on the voltages it receives from the electrode assembly 120. This means that there is no synthesis parameter to be fine-tuned, making the ECG device 100 easier to use.

If both the CR and CB electrodes are merged respectively as merged electrodes CRm and CBm and the electrode assembly 120 further includes m other precordial electrodes (where m is equal to 0, 1, 2, 3, or 4), the ECG device 100 may be able to generate up to 8+m modified leads using 3+m electrodes. These 8+m modified leads include 3 modified limb leads, 3 modified augmented limb leads, and 2+m modified precordial leads. If only one of the CR and CB electrodes is merged as a merged electrode CRm or CBm and the electrode assembly 120 further includes n other precordial electrodes (where n is equal to 0, 1, 2, 3, 4, or 5), the ECG device 100 may be able to generate 7+n modified leads using 3+n electrodes. These 7+n modified leads include 3 modified limb leads, 3 modified augmented limb leads, and 1+n modified precordial leads. In contrast, with 3 electrodes LA, RA, and LL and p other precordial electrodes (where p is equal to 0, 1, 2, 3, 4, 5, or 6), a conventional ECG device may be able to generate only up to 6+p leads. These 6+p leads include 3 limb leads, 3 augmented limb leads, and p precordial leads.

Apparently, because at least one of the CR and CB electrodes is merged as a merged electrode, the ECG device 100 of FIG. 1 is able to generate the same amount of leads with fewer electrodes. For example, if both the CR and CB electrodes are merged as merged electrodes CRm and CBm, it only takes 1 precordial electrode to generate 9 leads while the conventional ECG device requires 3 precordial electrodes. This means that the overall costs of the ECG device 100 may be relatively lower. In addition, because there are fewer electrodes to be attached to the patient's chest, the ECG device 100 is easier to use.

After conducting several experiments, it has been shown that the modified Wilson's central terminal Vw' is very similar to the Mason-Likar Wilson's central terminal Vw. As a result, substituting the latter with the former is a feasible approach. Even with the substitution, the modified precordial lead Vp' may still carry most of the information that the conventional precordial lead Vp would have carried, where p is equal to 1, 2, 3, 4, 5, or 6. In other words, just like the waveform of the conventional precordial lead Vp, the waveform of the modified precordial lead Vp' may also help a doctor make correct diagnosis.

In addition, the experiments have also shown that the modified limb leads I', II', and III', and the modified augmented limb leads aVR', aVL', and aVF' are very similar to the conventional limb leads I, II, and III, and the conventional augmented limb leads aVR, aVL, and aVF, respectively. As a result, substituting the latters with the formers is a feasible approach. Even with the substitution, the modified leads I', II', III', aVR', aVL', and aVF' may still carry most of the information that the conventional leads I, II, III, aVR, aVL, and aVF would have carried, respectively. In other words, just like the waveforms of the conventional leads I, II, III, aVR, aVL, and aVF, the waveforms of the modified leads I, II, III, aVR, aVL, or aVF may also help a doctor make correct diagnosis.

In the foregoing detailed description, the invention has been described with reference to specific exemplary embodiments thereof. It will be evident that various modifications may be made thereto without departing from the spirit and scope of the invention as set forth in the following claims. The detailed description and drawings are, accordingly, to be regarded in an illustrative sense rather than a restrictive sense.

What is claimed is:

1. An ECG lead signal generating circuit, comprising:
   a first precordial lead generator, configured to generate a first modified precordial lead according to three cardio enclosure voltages, wherein the three cardio enclosure voltages are sufficient for generating the first modified precordial lead; and
   a second precordial lead generator, configured to generate a second modified precordial lead according to the three cardio enclosure voltages, wherein the three cardio enclosure voltages are sufficient for generating the second modified precordial lead;
   wherein the ECG lead signal generating circuit is configured to receive the 3 cardio enclosure voltages and m precordial voltages to generate 8+m modified leads accordingly, where m is equal to 0, 1, 2, 3, or 4.

2. An ECG device comprising the ECG lead signal generating circuit of claim 1, wherein the ECG device further comprises:
   an electrode assembly, comprising three cardio enclosure electrodes for acquiring the three cardio enclosure voltages, respectively, wherein the first precordial lead generator and the second precordial lead generator are coupled to the electrode assembly;

wherein the electrode assembly further comprises m precordial electrodes for acquiring the m precordial voltages, where the ECG lead signal generating circuit is configured to generate the 8+m modified leads according to the 3 cardio enclosure voltages and the m precordial voltages.

3. An ECG lead signal generating circuit, comprising:

a first precordial lead generator, configured to generate a first modified precordial lead according to three cardio enclosure voltages, wherein the three cardio enclosure voltages are sufficient for generating the first modified precordial lead;

wherein the ECG lead signal generating circuit is configured to receive the 3 cardio enclosure voltages and n precordial voltages to generate 7+n modified leads accordingly, where n is equal to 0, 1, 2, 3, 4, or 5.

4. An ECG device comprising the ECG lead signal generating circuit of claim 3, wherein the ECG device further comprises:

an electrode assembly, comprising three cardio enclosure electrodes for acquiring the three cardio enclosure voltages, respectively, wherein the first precordial lead generator is coupled to the electrode assembly;

wherein the electrode assembly further comprises n precordial electrodes for acquiring the n precordial voltages, where the ECG lead signal generating circuit is configured to generate the 7+n modified leads according to the 3 cardio enclosure voltages and the n precordial voltages.

5. An ECG signal generating method, comprising:

generating a first modified precordial lead according to three cardio enclosure voltages, wherein the three cardio enclosure voltages are sufficient for generating the first modified precordial lead;

generating a second modified precordial lead according to the three cardio enclosure voltages, wherein the three cardio enclosure voltages are sufficient for generating the second modified precordial lead; and receiving m precordial voltages, where m is equal to 0, 1, 2, 3, or 4, and 8+m modified leads are generated according to the 3 cardio enclosure voltages and the m precordial voltages.

6. An ECG signal processing method comprising the ECG signal generating method of claim 5, wherein the ECG signal processing method further comprises:

acquiring the three cardio enclosure voltages from three cardio enclosure electrodes, respectively; and acquiring the m precordial voltages from m precordial electrodes.

7. An ECG signal generating method, comprising:

generating a first modified precordial lead according to three cardio enclosure voltages, wherein the three cardio enclosure voltages are sufficient for generating the first modified precordial lead; and receiving n precordial voltages, where n is equal to 0, 1, 2, 3, 4, or 5, and 7+n modified leads are generated according to the 3 cardio enclosure voltages and the n precordial voltages.

8. An ECG signal processing method comprising the ECG signal generating method of claim 7, wherein the ECG signal processing method further comprises:

acquiring the three cardio enclosure voltages from three cardio enclosure electrodes, respectively; and acquiring the n precordial voltages from n precordial electrodes.

9. An ECG device, comprising:

an electrode assembly, comprising three cardio enclosure electrodes for acquiring three cardio enclosure voltages, respectively, and a precordial electrode for acquiring a precordial voltage; and an ECG lead signal generating circuit, comprising:

a first precordial lead generator, coupled to the electrode assembly, configured to generate a first modified precordial lead according to the three cardio enclosure voltages but not according to the precordial voltage;

wherein the electrode assembly further comprises n precordial electrodes for acquiring n precordial voltages, where n is equal to 0, 1, 2, 3, 4, or 5, and the ECG lead signal generating circuit is configured to generate 7+n modified leads according to the 3 cardio enclosure voltages and the n precordial voltages.

10. An ECG signal processing method, comprising:

acquiring three cardio enclosure voltages from three cardio enclosure electrodes, respectively, and acquiring a precordial voltage from a precordial electrode;

generating a first modified precordial lead according to the three cardio enclosure voltages but not according to the precordial voltage; and acquiring n precordial voltages from n precordial electrodes, where n is equal to 0, 1, 2, 3, 4, or 5, and 7+n modified leads are generated according to the 3 cardio enclosure voltages and the n precordial voltages.

11. An ECG electrode assembly, comprising:

three cardio enclosure electrodes for acquiring three cardio enclosure voltages, wherein six modified leads and a modified precordial lead are able to be generated according to the three cardio enclosure voltages.

12. The ECG electrode assembly of claim 11, further comprising n precordial electrodes for acquiring n precordial voltages, where n is equal to 0, 1, 2, 3, 4, or 5, and 7+n modified leads are able to be generated according to the 3 cardio enclosure voltages and the n precordial voltages.

* * * * *